(12) United States Patent
Krimmer et al.

(10) Patent No.: US 6,492,544 B2
(45) Date of Patent: Dec. 10, 2002

(54) PROCESS FOR SYNTHESIS OF ENANTIOMERICALLY ENRICHED β-AMINO ACIDS

(75) Inventors: Hans-Peter Krimmer, Dietzenbach (DE); Karlheinz Drauz, Freigericht (DE); Jutta Lang, Alzenau (DE); Armin Boerner, Rostock (DE); Detlef Heller, Dettmannsdorf (DE); Jens Holz, Kessin (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/042,256

(22) Filed: Jan. 11, 2002

(65) Prior Publication Data

US 2002/0128509 A1 Sep. 12, 2002

(30) Foreign Application Priority Data

Jan. 11, 2001 (DE) .......................... 101 00 971

(51) Int. Cl.$^7$ ............................ C07C 229/08
(52) U.S. Cl. .................... 560/170; 560/155; 568/8; 568/12; 556/136
(58) Field of Search ................ 560/170, 155; 556/136; 568/8, 12

(56) References Cited

U.S. PATENT DOCUMENTS 6,172,249 B1 * 1/2001 Berens et al. .............. 556/14

FOREIGN PATENT DOCUMENTS

WO WO 99/59721 11/1999

OTHER PUBLICATIONS

K. Achiwa, et al., Tetrahedron Letters, No. 13, XP–002198461, pp. 1119–1120, "Catalytic Asymmetric Synthesis of Optically Active β–Amino Acids", 1978.

G. Zhu, et al., J. Org. Chem., vol. 64, No. 18, XP–002198462, pp. 6907–6910, "Highly efficient Asymmetric Synthesis of β–Amino Acid Derivatives via Rhodium–Catalyzed Hydrogenation of β(Acylamino) Acrylates", 1999.

W. D. Lubell, et al., Tetrahedron Asymmetry, vol. 2, No. 7, XP–001042293, pp. 543–554, "Enantioselective Synthesis of β–Amino Acids Based on Binap—Ruthenium (II) Catalyzed Hydrogenation", 1991.

D. Heller, et al., J. Org. Chem., vol. 66, No. 20, XP–002198463, pp. 6816–6817, "Pressure Dependent Highly Enantioselective Hydrogenation of Unsaturated β–Amino Acid Precursors", 2001.

Zhu et al, J. Org. Chem., vol. 64, pp. 6907–6910, 1999.*

* cited by examiner

Primary Examiner—Shailendra Kumar
(74) Attorney, Agent, or Firm—Oblon, Spivak, McClelland, Maier & Neustadt, P.C.

(57) ABSTRACT

Enantiomerically enriched N-acylated β-amino acids are synthesized by catalytic enantioselective hydrogenation of E-isomers and Z-isomers of 3-amino acrylic acid derivatives in the presence of a catalysts of formula (I)

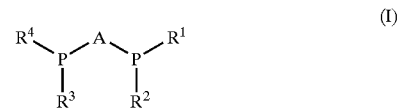

(I)

14 Claims, 1 Drawing Sheet

PROCESS FOR SYNTHESIS OF ENANTIOMERICALLY ENRICHED β-AMINO ACIDS

BACKGROUND OF THE INVENTION

1. Field of the Invention

The present invention relates to a process for the synthesis of a β-amino acid by enantioselective catalytic hydrogenation of a prochiral N-acetylated β-aminoacrylic acid.

2. Discussion of the Background

Because of their structural similarity to a-amino acids, β-amino acids may exhibit quasi-analogous behavior. Thus, intensive research in the chemical and pharmaceutical industry has been focused on β-amino acids with the aim to synthesize new bioactive agents with improved characteristics. One of the areas receiving attention is the enantioselective synthesis of β-amino acids.

In a recently published article (J. Org. Chem. 1999, 64, 6907), Zhang et al. describe the enantioselective catalytic hydrogenation of N-acylated β-aminoacrylic acids with rhodium catalysts carrying chiral ligands such as BICP and MeDuPHOS. The significance of the teaching by Zhang et al. is that relatively high hydrogen pressures and nonpolar aprotic solvents, among other factors, appear to be most favorable for the enantioselective catalytic hydrogenation. Furthermore, only the Rh-BICP complex yields high enantiomeric excesses for the corresponding Z-isomer at high pressures close to 20 bar, whereas the Rh-MeDuPHOS catalyst achieves only moderate to poor values.

Noyori et al. have also performed corresponding hydrogenation experiments (Tetrahedron: Asymmetry 1991, 2, 543554), albeit with less favorable results.

SUMMARY OF THE INVENTION

It is therefore an object of the present invention to provide a process for the synthesis of a β-amino acid that is readily applicable on an industrial scale and therefore superior to the known processes, particularly from the economic and ecological viewpoints.

It is another object of the present invention to provide a process for the synthesis of a β-amino acid that proceeds at a low hydrogen pressure and shorter hydrogenation times than known processes.

This and other objects have been achieved by the present invention the first embodiment which includes a process for synthesis of an enantiomerically enriched N-acylated β-amino acid, comprising:

enantioselectively catalytically hydrogenating a prochiral N-acylated β-aminoacrylic acid in a polar solvent;

wherein said by hydrogenating is carried out in the presence of a compound of formula (I)

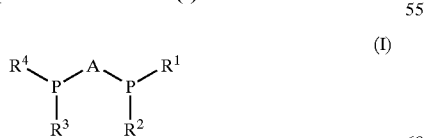

(I)

wherein
each of $R^1$, $R^2$, $R^3$, $R^4$ independently of one another represents $C_1$–$C_8$)-alkyl, ($C_2$–$C_8$)-alkoxyalkyl, ($C_6$–$C_{18}$)-aryl, ($C_7$–$C_{19}$)-aralkyl, ($C_3$–$C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_8$)-alkyl-($C_3$–$C_{18}$)-heteroaryl, ($C_3$–$C_8$)-cycloalkyl, ($C_{1-C8}$)-alkyl-($C_3$–$C_8$)-cycloalkyl or ($C_3$–$C_8$)-cycloalkyl-($C_1$–$C_8$)-alkyl; and A represents a ($C_2$–$C_5$)-alkylene bridge, a 1,2-($C_3$–$C_8$)-cycloalkylene bridge or a 1,3-($C_3$–$C_8$)-cycloalkylene bridge, which can contain one or more double bonds and/or can be substituted with one or more ($C_1$–$C_8$)-alkyl, ($C_1$–$C_8$)-aryl, ($C_1$–$C_8$)-alkoxy, ($C_2$–$C_8$)-alkoxyalkyl, ($C_6$–$C_{18}$)-aryl or ($C_3$–$C_3$)-cycloalkyl and/or can contain a hetero atom selected form the group consisting of N, O, P and S in said aryl ring;

with the proviso that A is not permitted to be a 2,2'-(1,1'-binaphthylene) group.

DETAILED DESCRIPTION OF THE INVENTION

Figure 1:
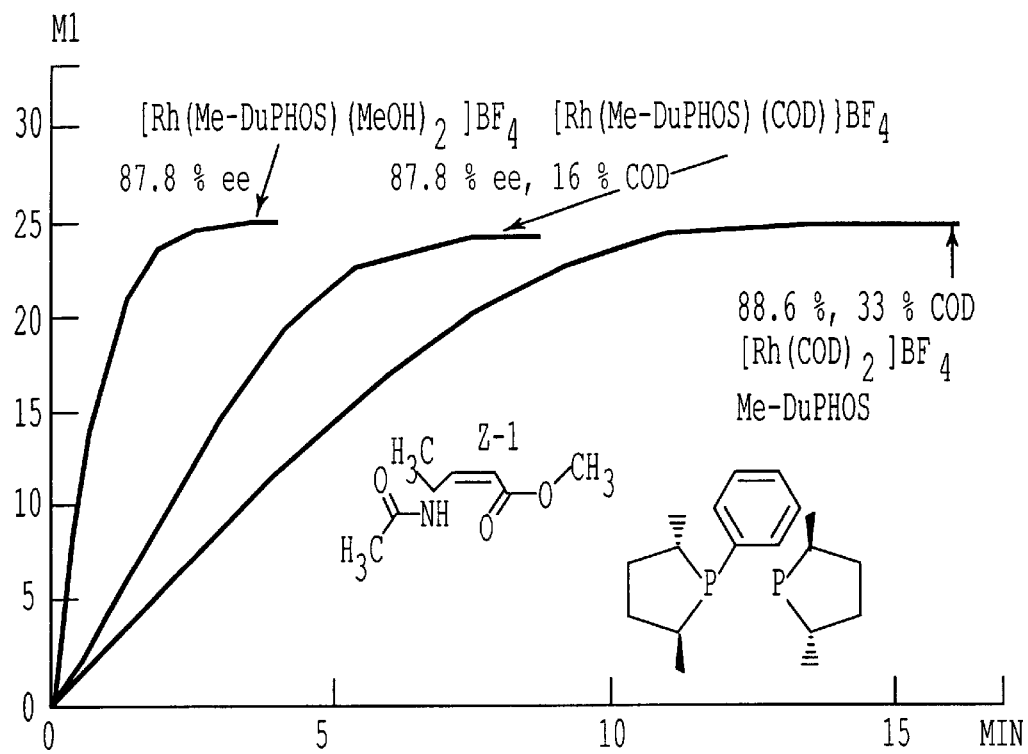
FIG. 1 shows how the hydrogenation proceeds over time.

A process that satisfies the above requirements is achieved in extremely simple but no less advantageous manner. Enantiomerically enriched N-acylated β-amino acids are synthesized by enantioselective catalytic hydrogenation of a prochiral N-acylated Z-β-aminoacrylic acids in a polar solvent. The process is carried out in the presence of a compound of formula (I),

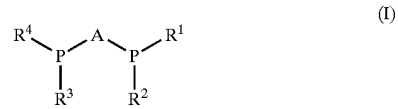

(I)

wherein
each of $R^1$, $R^2$, $R^3$, $R^4$ independently of one another denote ($C_1$–$C_8$)-alkyl, ($C_2$–$C_{11}$)-alkoxyalkyl, ($C_6$–$C_{18}$)-aryl, ($C_4$–$C_{19}$)-aralkyl, ($C_3$–$C_{18}$)-heteroaryl, ($C_4$–$C_{19}$)-heteroaralkyl, ($C_1$–$C_8$)-alkyl- ($C_6$–$C_{18}$)-aryl, ($C_1$–$C_8$)-alkyl-($C_3$–$C_{18}$)-heteroaryl, ($C_3$–$C_8$)-cycloalkyl, ($C_1$–$C_8$)-alkyl-($C_3$–$C_8$)-cycloalkyl, ($C_3$–$C_8$)-cycloalkyl-($C_3$–$C_8$)-cycloalkyl-($C_1$–$C_8$)-alkyl, and A denotes a ($C_2$–$C_5$)-alkylene bridge, a 1,2- or 1,3-($C_3$–$C_8$)-cycloalkylene bridge, which can contain one or more double bonds and/or can be substituted with one or more ($C_1$–$C_8$)-alkyl, ($C_1$–$C_8$)-acyl, ($C_1$–$C_8$)-alkoxy, ($C_2$–$C_8$)-alkoxyalkyl, ($C_6$–$C_{18}$)-aryl, ($C_3$–$C_8$)-cycloalkyl and/or can contain hetero atoms such as N, O, P and/or S in the ring, with the proviso that A is not permitted to be a 2,2'-(1,1'-binaphthylene) group. Above all, the process according to the present invention makes it possible to obtain the corresponding hydrogenation products in relatively short time and at lower pressures than in the known processes. Furthermore, in this process E-isomers and Z-isomers of the aforesaid prochiral N-acylated β-aminoacrylic acid are reacted at lower pressures and in shorter times than in the known processes. Comparably good enantiomeric excesses are obtained, thus making it possible to hydrogenate E/Z mixtures. It is this very aspect that is interesting for the industrial application of the process according to the present invention, because the stage of isomer separation before hydrogenation is now no longer necessary.

Preferably, the hydrogenation is carried out in the presence of compounds of formula (II),

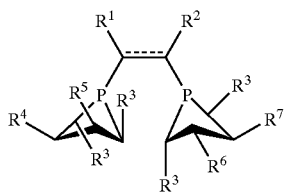

(II)

wherein
each of $R^1$, $R^2$, $R^4$, $R^5$, $R^6$, $R^7$ independently of one another denote ($C_1$–$C_8$)-alkyl, ($C_2$–$C_8$)-alkoxyalkyl, ($C_6$–$C_8$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_8$)-alkyl-($C_3$–$C_{18}$)-heteroaryl, ($C_3$–$C_8$)-cycloalkyl, ($C_1$–$C_8$)-alkyl-($C_3$–$C_8$)-cycloalkyl, ($C_3$–$C_8$)-cycloalkyl-($C_1$–$C_8$)-alkyl, or $R^2$ and $R^3$ are joined by a $C_2$–$C_5$-alkylene bridge, which can contain one or more double bonds and/or can be substituted with one or more ($C_1$–$C_8$)-alkyl, ($C_1$–$C_8$)-acyl, ($C_1$–$C_8$)-alkoxy, ($C_2$–$C_8$)-alkoxyalkyl, and/or can contain hetero atoms such as N, O, P and/or S in the ring, $R^3$ denotes ($C_1$–$C_8$)-alkyl, ($C_2$–$C_8$)-alkoxyalkyl, ($C_6$–$C_{18}$)-aryl, ($C_7$–$C_{19}$)-aralkyl, ($C_3$–$C_8$)-cycloalkyl, ($C_1$–$C_8$)-alkyl-($C_3$–$C_8$)-cycloalkyl.

Furthermore, preferred is a process in which an alcohol such as methanol, ethanol, isopropanol, butanol, or an ether such as MTBE, THF, an ester such as acetic ester, acetoacetic ester, or an halogenated solvent such as chloroform, methylene chloride, or any desired mixture thereof is used as the polar solvent. It is immaterial to the present invention whether the polar solvent molecules which act as ligands in the catalyst, are identical to the solvent being used. It is also possible to use different solvents.

In the process of the present invention, it is possible to convert E/Z mixtures of a prochiral N-acylated Z-β-aminoacrylic acid in shorter time than in the known processes. This is particularly advantageous because such mixtures are often encountered in the synthesis of the corresponding acrylic acid derivatives, and otherwise would have to be separated laboriously. This additional step is unnecessary in the present invention. It is precisely this aspect that is advantageous for application of the process to the industrial scale, because saving of a production step or a purification step always helps to lower the manufacturing costs.

Transition metals are preferred as the central atom in the catalyst for the hydrogenation reaction. Particularly preferred is a process in which a complex containing the transition metals Rh, Ru, Co and/or Ir, in uncharged or ionic form, is used as a catalyst.

It is most particularly advantageous to use complexes which contain at least one polar solvent molecule as ligand in their ligand sphere. Thereby faster exchange is achieved between ligand (polar solvent molecule) and substrate to be hydrogenated, thus also greatly shortening the hydrogenation times (FIG. 1).

The use of ligands and complexes takes place in the form of transfer hydrogenation ("Asymmetric transfer hydrogenation of C=O and C=N bonds", M. Wills et al., Tetrahedron: Asymmetry 1999, 10, 2045; "Asymmetric transfer hydrogenation catalyzed by chiral ruthenium complexes", R. Noyori et al., Acc. Chem. Res. 1997, 30, 97; "Asymmetric catalysis in organic synthesis", R. Noyori, John Wiley & Sons, New York, 1994, p. 123; "Transition metals for organic synthesis", Eds. M. Beller, C. Bolm, Wiley-VCH, Weinheim, 1998, Vol. 2, p. 97; "Comprehensive Asymmetric Catalysis", Eds.: Jacobsen, E. N.; Pfaltz, A.; Yamamoto, H., Springer-Verlag, 1999), although it can also be achieved in the classical manner with elemental hydrogen. Accordingly, the process can operate both, by hydrogenation with hydrogen gas or by transfer hydrogenation.

For enantioselective hydrogenation, the preferred procedure is to dissolve the substrate to be hydrogenated and the catalyst, such as [Rh(MeDuPHOS) (MeOH)$_2$]BF$_4$ in the polar solvent.

Preferably the catalyst will be formed from a precatalyst such as [Rh(COD)$_2$]BF$_4$ by prehydrogenation in the polar solvent in the presence of the chiral ligand, before the substrate is added. Thereafter hydrogenation will be performed at a hydrogen pressure of 0.1 to 10 bar, preferably 0.5 to 5 bar. The pressure includes all values and subvalues therebetween especially including 0.5, 1, 1.5, 2, 2.5, 3, 3.5, 4, 4.5, 5, 5.5, 6, 6.5, 7, 7.5, 8, 8.5, 9 and 9.5 bar. The temperature for hydrogenation must be chosen such that the reaction proceeds sufficiently rapidly to the desired enantiomeric excesses, while secondary reactions are prevented as much as possible. Preferably, the process takes place at temperatures of −20° C. to 100° C., more preferably at 0° C. to 50° C. The temperature includes all values and subvalues therebetween especially including −10, 0, 10, 20, 30, 40, 50, 60, 70, 80 and 90° C.

The ratio of substrate to catalyst is determined by economic considerations. The reaction must be performed sufficiently rapidly at the lowest possible catalyst concentration. It is preferable, however, to operate at a substrate to catalyst ratio of between 10000:1 and 10:1, preferably 1000:1 and 50:1. The substrate to catalyst ratio includes all values and subvalues therebetween especially including 9000:1, 8000:1, 7000:1, 6000:1, 5000:1, 4000:1, 3000:1, 2000:1, 1000:1, 900:1, 800:1, 700:1, 600:1, 500:1, 400:1, 300:1, 200:1, 100:1, 90:1, 80:1, 70:1 and 60:1.

In a further embodiment, the invention relates to a process for synthesis of β-amino acids by elimination of the protective group of N-acylated β-amino acids synthesized by the process of the present invention.

A further aspect of the present invention relates to the use of β-amino acids synthesized according to the present invention for organic syntheses, especially for synthesis of bioactive agents.

Compound (I) can be endowed with greater molecular weight by binding to a polymer, and thereby can be made heterogeneous, if necessary. Enantioselective hydrogenation with substrates having molecular weight increased in this way can therefore take place in the homogeneous and heterogeneous phase. This binding can in principle be achieved in a manner known to those skilled in the art. Advantageously, binding in formula (II) takes place via the substituents $R^1$ or $R^2$, although it can take place at another position in the molecule. This will depend on the interaction which the polymer binding exerts on the enantioselective reaction, and which can be determined in routine experiments. It is therefore advantageous to couple the compounds according to the present invention via a linker to a suitable polymer, in order to preclude detrimental interactions between polymer and complex that could influence the catalytic reaction. Preferred linkers, the method for binding to the polymer and complex, and also suitable polymers can be found in German Patents 10029601, 10003110, 10002973 and 10002976 which are incorporated herein by reference in their entirety. With its molecular weight increased in this way, the complex or ligand (I) or (II) can be used particularly advantageously in a membrane reactor, thus creating the possibility of a quasi-continuous or continuous catalytic reaction (German Patent 19910691.6; Wandrey et al., Tetrahedron Asymmetry 1999, 10, 923–928). A particular advantage is achieved thereby in terms of costs, especially on the industrial scale.

In general, the β-amino acid precursors were synthesized according to procedures in the literature. For the synthesis of the compounds, the general procedures of Zhang et al. (G. Zhu, Z. Chen, X. Zhang, J. Org. Chem. 1999, 64, 6907–6910) and Noyori et al. (W. D. Lubell, M. Kitamura, R. Noyori, Tetrahedron: Asymmetry 1991, 2, 543–554) as well as Melillo et al. (D. G. Melillo, R. D. Larsen, D. J. Mathre, W. F. Shukis, A. W. Wood, J. R. Colleluori, J. Org. Chem. 1987, 52, 5143–5150) can be used for guidance. Starting from the corresponding 3-ketocarboxylic acid esters, the desired prochiral enamides are obtained by reaction with ammonium acetate followed by acylation. The hydrogenation products can be converted to the β-amino acids by methods that are analogous to those used for α-amino acids.

The following table shows the superior results of the process in the hydrogenation presented below (FIG. 1):

|  | Zhang et al. | Process of the Present Invention |
|---|---|---|
| Catalyst | [Rh(COD)$_2$]BF$_4$ + MeDuPHOS | [Rh(MeDuPHOS)(MeOH)$_2$]BF$_4$ |
| Solvent | Toluene | Methanol |
| Pressure | about 20 bar | 1 bar |
| Time | 24 h | 5 min (t$_{1/2}$ = 1.3 min) |
| Yield [%] | 100 | 100 |
| ee [%] | 63.7 | 88 |

Figure 2:
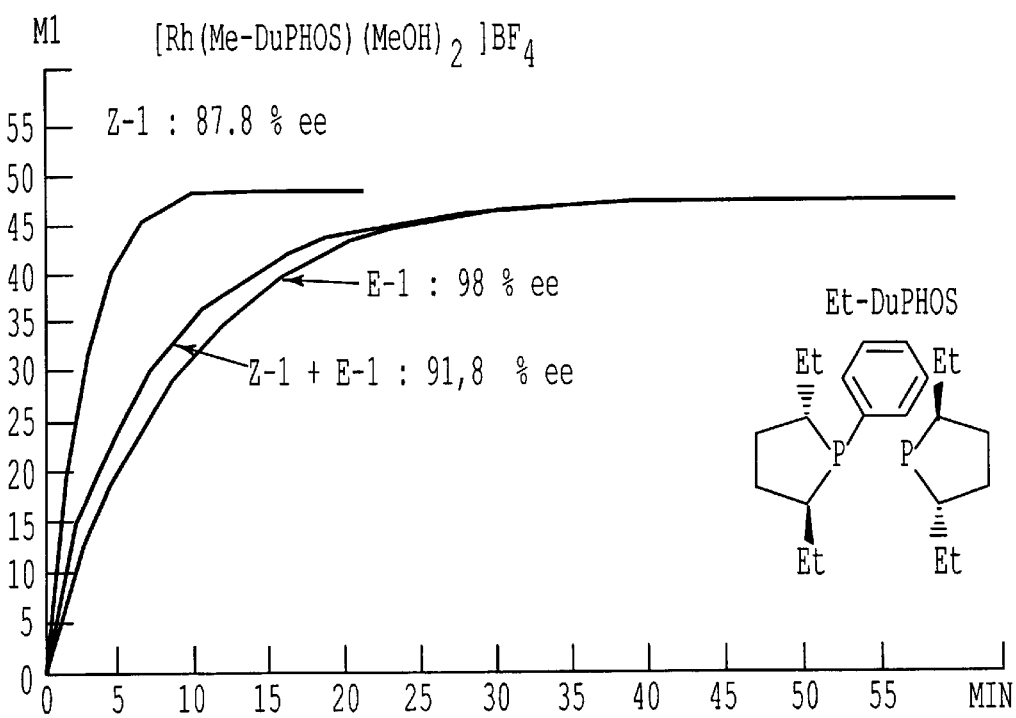
FIG. 2 shows how the hydrogenation proceeds over time.

In contrast to the known processes, in the process of the present invention, Z-isomers of the N-acylated β-aminoacrylic acids can also be hydrogenated with high enantioselectivity, in a short time, at low pressures, using the catalyst system of the present invention: [Rh(alkDuPHOS)(MeOH)$_2$]BF$_4$, wherein alk is preferably Et or Me. Consequently the E/Z mixtures can also be used for hydrogenation, without any concern about the known disadvantages for hydrogenation of the Z components with this type of complex. The reaction of E/Z-N-acetyl-3-aminoacrylic acid methyl ester in the methanol/[Rh(EtDuPHOS)(MeOH)$_2$]BF$_4$ system at 25° C. and a hydrogen pressure of 1 bar produced a 100% yield of the N-acylated β-amino acid ester with an ee value of 92% within 5 minutes (FIG. 2).

Preferred examples of ($C_1$–$C_8$)-alkyl groups are methyl, ethyl, n-propyl, isopropyl, n-butyl, isobutyl, sec-butyl, tert-butyl, pentyl, hexyl, heptyl or octyl as well as all of their bond isomers. Preferred ($C_1$–$C_8$)-alkoxy groups are methoxy, ethoxy, n-propoxy, iso-propoxy, n-butoxy, isobutoxy, sec-butoxy, tert-butoxy, pentoxy, hexoxy, heptoxy, octyloxy and their bond isomers. The ($C_2$–$C_8$)-alkoxyalkyl group is to be understood as a group in which the alkyl chain is interrupted by at least one oxygen function, although two oxygen atoms cannot be joined to one another. The number of carbon atoms indicates the total number of carbon atoms contained in the group. A ($C_2$–$C_5$)-alkylene bridge is a carbon chain containing two to five C atoms, this chain being bonded to the molecule in question via two of its C atoms, which must be different. The groups just described can be substituted with one or more halogen atoms and/or with one or more groups that contain a N, O, P, S and/or Si atoms. These are in particular alkyl groups of the foregoing type, which contain one or more of these hetero atoms in their chain or which are bonded to the molecule via one of these hetero atoms.

A ($C_3$–$C_8$)-cycloalkyl is preferably a cyclopropyl, a cyclobutyl, a cyclopentyl, a cyclohexyl and a cycloheptyl group, etc. These can be substituted with one or more halogen atoms and or a group containing a N, O, P, S and/or Si atom, and/or can contain a N, O, P and/or S atoms in the ring, examples being 1-, 2-, 3- ,4-piperidyl, 1-, 2-, 3-pyrrolidinyl, 2-, 3-tetrahydrofuryl, 2-, 3-, 4-morpholinyl.

A ($C_3$–$C_8$)-cycloalkyl-($C_1$–$C_8$)-alkyl group denotes a cycloalkyl group such as described hereinabove, which is bound to the molecule via an alkyl group such as specified hereinabove.

Within the scope of the present invention, ($C_1$–$C_8$)-acyloxy denotes an alkyl group such as defined hereinabove with at most 8 C atoms, which is bound to the molecule via a COO function.

Within the scope of the present invention, ($C_1$–$C_8$)-acyl denotes an alkyl group such as defined hereinabove with at most 8 C atoms, which is bound to the molecule via a CO function.

A ($C_6$–$C_{18}$)-aryl group is understood to be an aromatic group with 6 to 18 carbon atoms. Preferred examples are groups such as phenyl, naphthyl, anthryl, phenanthryl and biphenyl or systems of such type that are annelated to the molecule in question. Preferred examples are indenyl systems, which may be substituted with ($C_1$–$C_8$)-alkyl, ($C_1$–$C_8$)-alkoxy, $NR^1R^2$, ($C_1$–$C_8$)-acyl, ($C_1$–$C_8$)-acyloxy.

A ($C_7$–$C_{19}$)-aralkyl group is a ($C_6$–$C_{18}$)-aryl group bonded to the molecule via a ($C_1$–$C_8$)-alkyl group.

Within the scope of the invention, a ($C_3$–$C_{18}$)-heteroaryl group designates a five-membered, six-membered or seven-membered aromatic ring system comprising 3 to 18 C atoms and containing hetero atoms such as nitrogen, oxygen or sulfur in the ring. In particular, groups such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acrinyl, quinolinyl, phenanthridiyl, 2-, 4-, 5-, 6-pyrimidinyl are regarded as such heteroatoms.

A ($C_4$–$C_{19}$)-heteroalkyl is understood to be a heteroaromatic system corresponding to the ($C_7$–$C_{19}$)-aralkyl group.

Fluorine, chlorine, bromine and iodine are used as halogens (Hal).

PEG denotes polyethylene glycol.

Within the scope of the invention, the term enantiomerically enriched means that the proportion of one enantiomer in the mixture with its optical antipode ranges from >50% to <100%. The proportion of the enantiomer includes all values and subvalues therebetween especially including 55, 60, 65, 70, 75, 80, 85, 90 and 95%. The ee value is calculated as follows:

([enantiomer 1]−[enantiomer 2])/([enantiomer 1]+[enantiomer 2])= ee value.

Within the scope of the present invention, the complexes according to the present invention and ligands encompass all possible diastereoisomers. The two optical antipodes of any given diastereoisomer are also included in the designation.

The catalysts described herein determine, with their configuration, the optical induction in the product. The catalysts used in racemic form also yield racemic products.

Subsequent resolution of the racemate then yields the enantiomerically enriched products once again.

N-acyl groups are understood to be protective groups which in general are used as standard agents in amino acid chemistry for protection of nitrogen atoms. They include preferably formyl, acetyl, Moc, Eoc, phthalyl, Boc, Alloc, Z, Fmoc, etc.

The broken line in formula (II) denotes an optional double bond.

Having generally described this invention, a further understanding can be obtained by reference to certain specific examples which are provided herein for purposes of illustration only, and are not intended to be limiting unless otherwise specified.

EXAMPLES

Standard Hydrogenation Experiment 1.0 mmol of the prochiral olefin is melted in a 1.5 ml glass ampule in 1 ml of solvent under anaerobic conditions. The ampule and 0.01 mmol of the corresponding catalyst complex (usually as [Rh(MeDuPHOS)COD]BF$_4$) are introduced under argon into a thermostatted (usually at 25° C.) hydrogenation reactor equipped with a magnetic stirrer. Thereafter 15.0 ml of solvent such as methanol is added. After gas exchange of argon by hydrogen, the precatalyst is first converted to the solvent complex which is actually catalytically active by prehydrogenation of the diolefin. The asymmetric hydrogenation is started by breaking the glass ampule containing the substrate using the bar magnet of the stirrer. The hydrogen consumption with time, under isobaric conditions at a total pressure of 1.0 kgf/cm$^2$, is followed as measured variable proportional to the product, using an automatically recording gas-consumption measuring apparatus.

The product analysis is then performed by GC or HPLC, depending on the substrate.

Explanation of FIG. 2:

Hydrogenation of a 1:1 Z-1/E-1 mixture with the Et-DuPHOS system. 1.0 mmol of each, compared with the hydrogenation of 2.0 mmol of Z-1 and 2.0 mmol of E-1; otherwise standard conditions.

German patent application 101 00 971.2 filed Jan. 11, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for synthesis of an enantiomerically enriched N-acylated -amino acid, comprising:

enantioselectively catalytically hydrogenating a prochiral N-acylated P-aminoacrylic acid in a polar solvent;

wherein said by hydrogenating is carried out in the presence of a compound of formula (I)

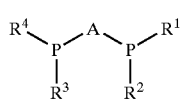

(I)

wherein
each of R$^1$, R$^2$, R$^3$, R$^4$ independently of one another represents (C$_1$–C$_8$)-alkyl, (C$_2$–C$_8$)-alkoxyalkyl, (C$_6$–C$_{18}$)-aryl, (C$_7$–C$_{19}$)-aralkyl, (C$_3$–C$_{18}$)-heteroaryl, (C$_4$–C$_{19}$)-heteroaralkyl, (C$_1$–C$_8$)-alkyl-(C$_6$–C$_{18}$)-aryl, (C$_1$–C$_8$)-alkyl-(C$_3$–C$_{18}$)-heteroaryl, (C$_3$–C$_8$)-cycloalkyl, (C$_1$–C$_8$)-alkyl-(C$_3$–C$_8$)-cycloalkyl or (C$_3$–C$_8$)-cycloalkyl-(C$_1$–C$_8$)-alkyl; and A represents a (C$_2$–C$_5$)-alkylene bridge, a 1,2-(C$_3$–C$_8$)-cycloalkylene bridge or a 1,3-(C$_3$–C$_8$)-cycloalkylene bridge, which can contain one or more double bonds and/or can be substituted with one or more (C$_1$–C$_8$)-alkyl, (C$_1$–C$_8$)-aryl, (C$_1$–C$_8$)-alkoxy, (C$_2$–C$_8$)-alkoxyalkyl, (C$_6$–C$_{18}$)-aryl or (C$_3$–C$_8$)-cycloalkyl and/or can contain a hetero atom selected from the group consisting of N, O, P and S in said aryl ring;

with the proviso that A is not permitted to be a 2,2'-(1,1'-binaphthylene) group.

2. The process according to claim 1, wherein said hydrogenating is carried out in the presence of a compound of formula (II)

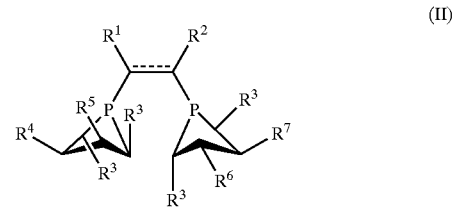

(II)

wherein
each of R$^1$, R$^2$, R$^4$, R$^5$, R$^6$, R$^7$ independently of one another represents (C$_1$–C$_8$)-alkyl, (C$_2$–C$_8$)-alkoxyalkyl, (C$_6$–C$_{18}$)-aryl, (C$_7$–C$_{19}$)-aralkyl, (C$_3$–C$_{18}$)-heteroaryl, (C$_4$–C$_{19}$)-heteroaralkyl, (C$_1$–C$_8$)-alkyl-(C$_6$–C$_{18}$)-aryl, (C$_1$–C$_{19}$)-alkyl-(C$_3$–C$_{18}$)-heteroaryl, (C$_3$–C$_8$)-cycloalkyl, (C$_1$–C$_8$)-alkyl-(C$_3$–C$_8$)-cycloalkyl or (C$_3$–C$_8$)-cycloalkyl-(C$_1$–C$_8$)-alkyl; or R$^2$ and R$^3$ are joined by a (C$_2$–C$_8$)-alkylene bridge, which can contain one or more double bonds and/or can be substituted with one or more (C$_1$–C$_8$)-alkyl, (C$_1$–C$_8$)-aryl, (C$_1$–C$_8$)-alkoxy or (C$_2$–C$_8$)-alkoxyalkyl, and/or can contain a hetero atom selected from the group consisting of N, O, P and S in the aryl ring; and R$^3$ denotes (C$_1$–C$_8$)-alkyl, (C$_2$–C$_8$)-alkoxyalkyl, (C$_6$–C$_{18}$)-aryl, (C$_7$–C$_{19}$)-aralkyl, (C$_3$–C$_8$)-cycloalkyl or (C$_1$–C$_8$)-alkyl-(C$_3$–C$_8$)-cycloalkyl.

3. The process according to claim 1, wherein an alcohol, an ether, an ester, a halogenated solvent or a mixture thereof is used as said polar solvent.

4. The process according to claim 1, wherein an E/Z mixture of said prochiral N-acylated β-aminoacrylic acid is used for said hydrogenating.

5. The process according to claim 1, wherein a complex containing a transition metal selected from the group consisting of Rh, Ru, Co and Ir is used as a catalyst.

6. The process according to claim 1, wherein a catalyst which contains at least one polar solvent molecule as ligand is used.

7. The process according to claim 1, wherein said hydrogenating is performed with hydrogen gas or by transfer hydrogenation.

8. The process according to claim 7, wherein said hydrogenating is performed at a hydrogen pressure of 0.1 to 10 bar.

9. The process according to claim 8, wherein said hydrogen pressure is 0.5 to 5 bar.

10. The process according to claim 1, wherein said hydrogenating occurs at a temperature of −20° C. to 100° C.

11. The process according to claim 10, wherein said temperature is 0° C. to 50° C.

12. The process according to claim 1, wherein a substrate to catalyst ratio is between 10000:1 and 10:1.

13. The process according to claim 12, wherein said substrate to catalyst ratio is between 1000:1 and 50:1.

14. A process for the synthesis of a β-amino acid, comprising:

eliminating the protective group of a N-acylated β-amino acid obtained by the process of claim 1.

* * * * *